United States Patent
Nakamura

(10) Patent No.: US 11,397,157 B2
(45) Date of Patent: Jul. 26, 2022

(54) WATER-CONTAINING SUBSTANCE DETECTION DEVICE, WATER-CONTAINING SUBSTANCE DETECTION METHOD, AND METHOD OF MANUFACTURING RUBBERY POLYMER

(71) Applicant: ZEON CORPORATION, Tokyo (JP)

(72) Inventor: Masao Nakamura, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 301 days.

(21) Appl. No.: 16/497,034

(22) PCT Filed: Mar. 26, 2018

(86) PCT No.: PCT/JP2018/012185
§ 371 (c)(1),
(2) Date: Sep. 24, 2019

(87) PCT Pub. No.: WO2018/181199
PCT Pub. Date: Oct. 4, 2018

(65) Prior Publication Data
US 2020/0378913 A1    Dec. 3, 2020

(30) Foreign Application Priority Data
Mar. 30, 2017 (JP) .............................. JP2017-069253

(51) Int. Cl.
*G01J 5/48*      (2022.01)
*G01N 25/56*   (2006.01)
(Continued)

(52) U.S. Cl.
CPC .............. *G01N 25/56* (2013.01); *C08C 2/06* (2013.01); *G01J 5/48* (2013.01); *G01N 33/445* (2013.01)

(58) Field of Classification Search
CPC ........ G01N 25/56; G01N 25/58; B65G 47/70; B65G 47/71; B65G 47/715; B65G 47/72;
(Continued)

(56) References Cited

U.S. PATENT DOCUMENTS

| 6,444,936 B1* | 9/2002 | Ludwig ................. B07C 5/3425 |
| | | 198/370.1 |
| 2008/0257795 A1* | 10/2008 | Shuttleworth ............ B07C 5/36 |
| | | 209/576 |

FOREIGN PATENT DOCUMENTS

| JP | S59-012339 A | 1/1984 |
| JP | H02-209419 A | 8/1990 |

(Continued)

OTHER PUBLICATIONS

Jun. 26, 2018 Search Report issued in International Patent Application No. PCT/JP2018/012185.
(Continued)

*Primary Examiner* — Herbert K Roberts
(74) *Attorney, Agent, or Firm* — Oliff PLC

(57) ABSTRACT

A water-containing substance detection device that detects a water-containing rubbery polymer, includes a conveyor configured to convey rubbery polymers; and a detector configured to detect the water-containing rubbery polymer among the rubbery polymers, conveyed by the conveyor, by a temperature sensor. The conveyor has a surface with an emissivity of 0.50 or more. The temperature sensor has a frame rate falling within a range of 5 Hz to 120 Hz. The detector detects the water-containing rubbery polymer, near an ejection port of the conveyor, and on a downstream side of the ejection port.

10 Claims, 6 Drawing Sheets

(51) Int. Cl.
*G01N 33/44* (2006.01)
*C08C 2/06* (2006.01)

(58) Field of Classification Search
CPC ...... B65G 47/74; B65G 47/76; B65G 47/763;
B65G 47/766; B65G 47/78; B65G 11/12;
B65G 11/123; C08C 2/06; C08J 3/12;
B29B 9/02; Y02W 30/62; B07B 13/16;
B07C 5/362
See application file for complete search history.

(56) References Cited

FOREIGN PATENT DOCUMENTS

| | | |
|---|---|---|
| JP | H03-089980 A | 4/1991 |
| JP | H04-136094 U | 12/1992 |
| JP | 3075064 U | 2/2001 |
| JP | 2002-267432 A | 9/2002 |
| JP | 2005-106748 A | 4/2005 |
| JP | 2005106748 A * | 4/2005 |
| JP | 2009-031099 A | 2/2009 |
| JP | 2009031099 A * | 2/2009 |
| JP | 2010-164407 A | 7/2010 |
| JP | 2014-153055 A | 8/2014 |
| JP | 2017015514 A * | 1/2017 |

OTHER PUBLICATIONS

Jun. 25, 2021 Office Action issued in Chinese Patent Application No. 201880019745.9.
Jul. 13, 2021 Office Action issued in Japanese Patent Application No. 2019-509819.
Dec. 7, 2021 Office Action issued in Japanese Patent Application No. 2019-509819.

* cited by examiner

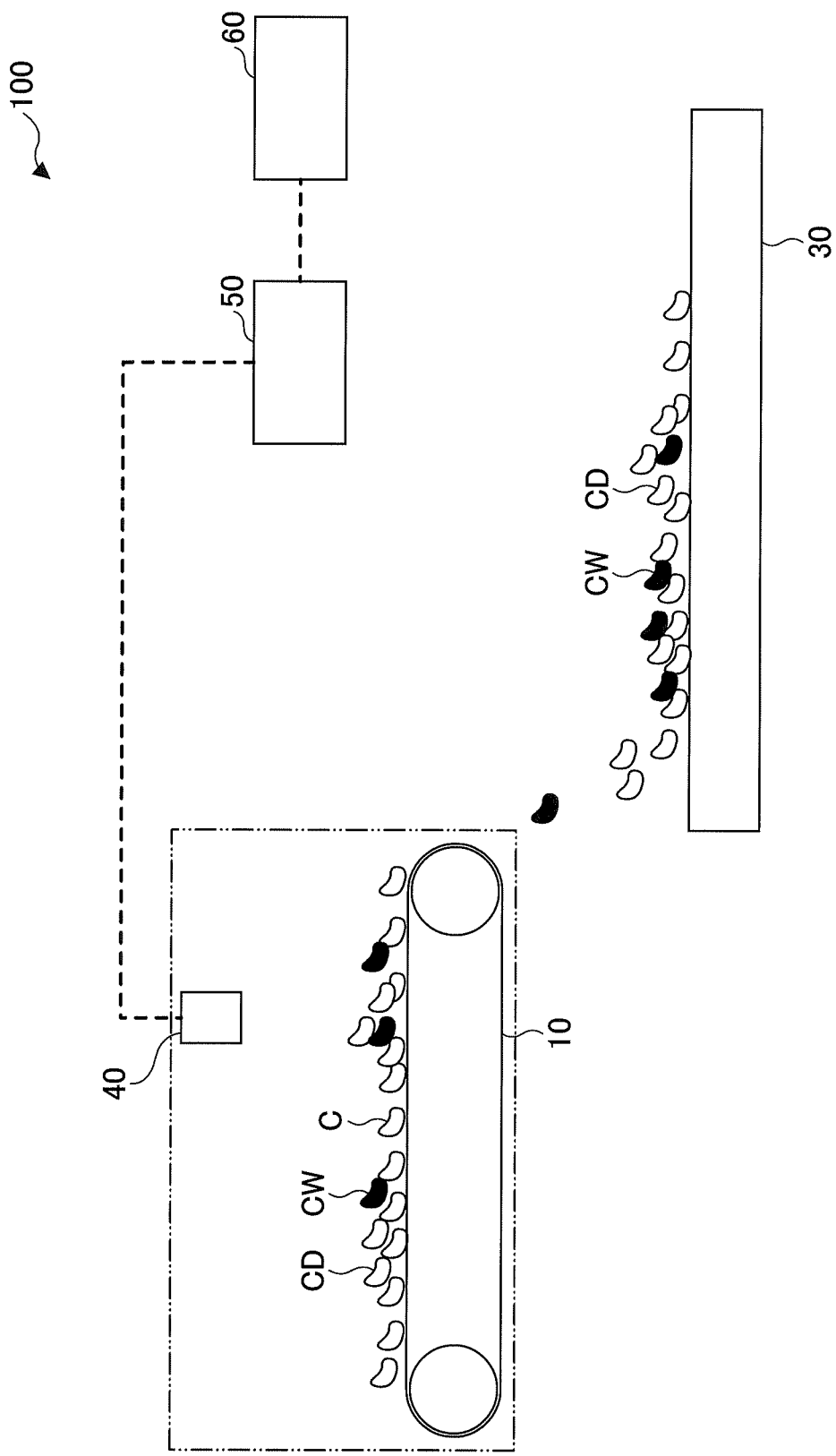

WATER-CONTAINING SUBSTANCE DETECTION DEVICE, WATER-CONTAINING SUBSTANCE DETECTION METHOD, AND METHOD OF MANUFACTURING RUBBERY POLYMER

BACKGROUND OF THE INVENTION

1. Field of the Invention

The present invention relates to a water-containing substance detection device, a water-containing substance detection method and a method of manufacturing rubbery polymer.

2. Description of the Related Art

In a process of manufacturing rubbery polymer, the rubbery polymer after polymerization and solidification includes a large amount of water. The rubbery polymer is subjected to an extrusion-drying process. Then, by performing a vibration drying process for obtained crumbs of rubbery polymer, the crumbs of rubbery polymer are further heated and dried, thereby water in the rubbery polymer is removed. Sometimes a water-containing substance such as an undried crumb (or insufficiently dried) contained in the dried rubbery polymer is detected, and such a water-containing substance is removed from the dried rubbery polymer.

For example, Patent document 1 discloses detecting water contained in a crumb-shaped rubber by using an infrared sensor.

CITATION LIST

Patent Literature

[PTL 1] Japanese Unexamined Patent Application Publication No. S59-12339

SUMMARY OF THE INVENTION

Problem to be Solved by the Invention

However, in the related art, the surface of the conveyor is often erroneously recognized as a water-containing substance due to the lower temperature of the surface of the conveyor detected by the infrared sensor. Moreover, when an amount of processing for the rubbery polymer is great, only an outermost surface of the rubbery polymer is detected. Thus, a water-containing substance is not detected with greater accuracy. Accordingly, in the related art, an enhancement of a product quality is limited.

The present invention aims to provide a water-containing substance detection device that detects a water-containing substance in a rubbery polymer with greater accuracy.

Means for Solving Problems

In order to solve the problem, according to an aspect of the present invention, a water-containing substance detection device, that detects a water-containing rubbery polymer, includes a conveyor configured to convey rubbery polymers; and a detector configured to detect the water-containing rubbery polymer among the rubbery polymers, conveyed by the conveyor, by a temperature sensor. The conveyor has a surface with an emissivity of 0.50 or more. The temperature sensor has a frame rate falling within a range of 5 Hz to 120 Hz. The detector detects the water-containing rubbery polymer, near an ejection port of the conveyor, and on a downstream side of the ejection port.

Effect of Invention

According to an aspect of the present invention, a water-containing substance detection device that more accurately detects a water-containing substance in a rubbery polymer is provided.

BRIEF DESCRIPTION OF THE DRAWINGS

FIG. 6 is a diagram depicting an example of the water-containing substance detection device according to the related art.

DETAILED DESCRIPTION OF THE PREFERRED EMBODIMENTS

Figure 1:
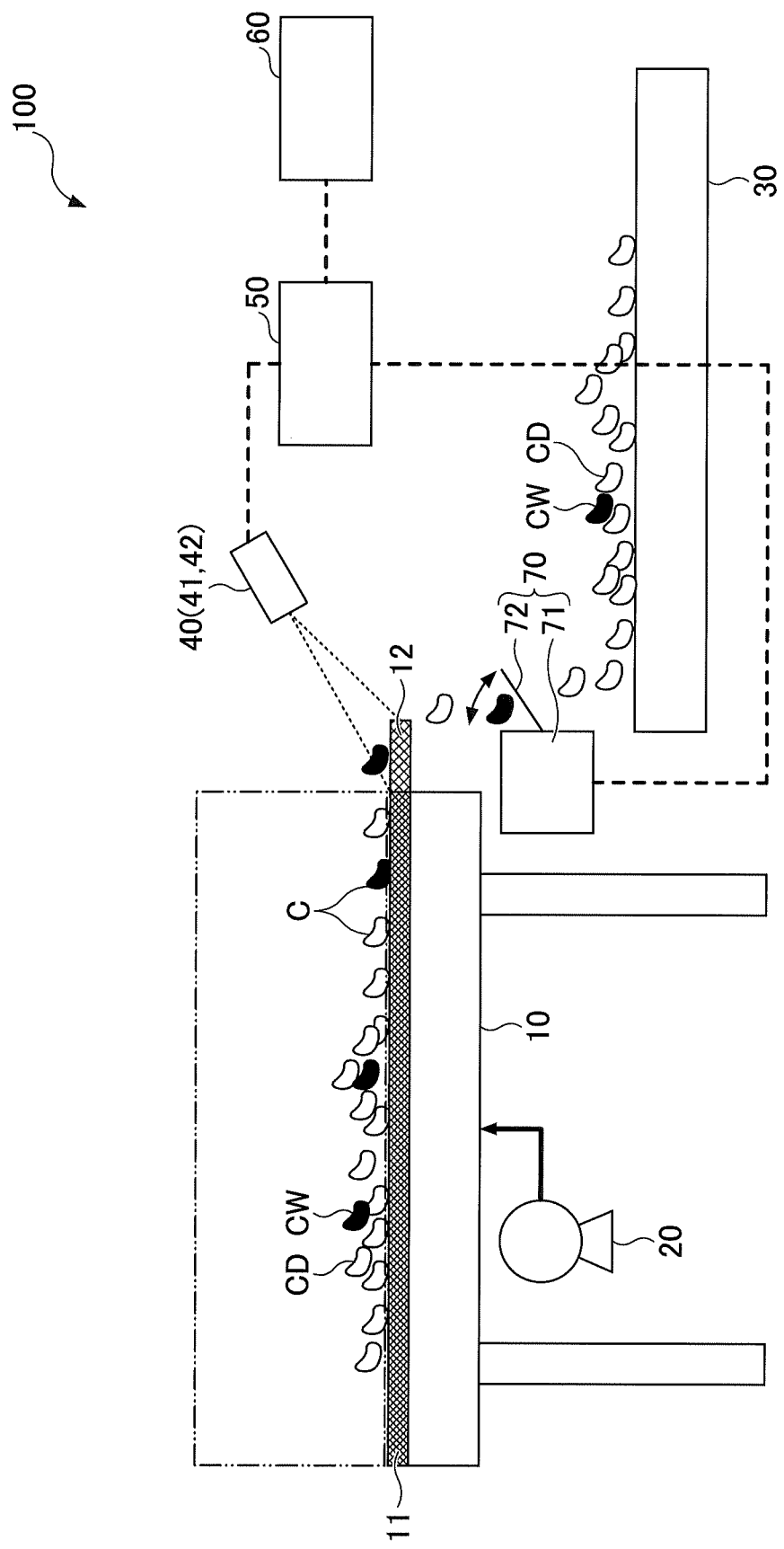
FIG. 1 is a diagram schematically depicting an example of a water-containing substance detection device according to a first embodiment of the present invention.

In the following, with reference to drawings, embodiments of the present invention will be illustratively described in detail. Note that in the embodiment, to a component common in the drawings, the same reference numeral or a corresponding reference numeral is assigned, and an explanation of the component will be omitted.

FIG. 1 is a diagram schematically depicting an example of a water-containing substance detection device according to a first embodiment of the present invention. A crumb detection device 100 according to the embodiment is a water-containing substance detection device that detects a water-containing substance contained in a rubbery polymer. The rubbery polymer in the embodiment refers to a plurality of crumbs C formed through a drying process. The plurality of crumbs C include dried crumbs CD that do not contain water, and water-containing crumbs CW that contain water. The crumb detection device 100 is an example of the water-containing substance detection device according to the present invention.

The crumb detection device 100 includes a conveyor 10 that conveys crumbs C, as illustrated in FIG. 1. A configuration of the conveyor 10 is not particularly limited. The conveyor 10 according to the embodiment may be a belt-type conveyor or may be a vibration-type conveyer. In the vibration-type conveyor, each crumb C is easily turned upside down during conveyance, and therefore easily detected. A material of the conveyor 10 is not particularly limited. When a vibration-type conveyor is used, a stainless steel plate having a surface coated with Teflon (trademark registered) is preferably used. The conveyor 10 is an example of a conveyor in the water-containing substance detection device according to the present invention.

In the embodiment, the conveyor 10 has a surface 11 with an emissivity of 0.50 or more. Emissivity refers to a value representing a degree of radiation of infrared energy from a surface of an article. For example, an emissivity of a mirror is zero, and an emissivity of a perfect black body is one.

In the embodiment, the emissivity of the surface 11 of the conveyor 10 is 0.50 or higher, preferably 0.70 or higher, more preferably 0.80 or higher. When the emissivity of the surface 11 of the conveyor 10 is extremely low, more light is reflected from the surface 11 of the conveyor 10, and the detection sensitivity of a sensor 40 may be significantly decreased. Although the conveyor 10 may be made of stainless steel, as described above, and the emissivity of the stainless steel is about 0.3, the emissivity of the surface of the conveyor 10 is 0.50 or more, because the surface of the conveyor 10 is coated with, for example Teflon.

Moreover, the crumb detection device 100 includes the sensor 40 that detects the crumbs C, as illustrated in FIG. 1. An infrared camera 41 is installed in the sensor 40. The infrared camera 41 in the sensor 40 detects the temperature of the crumbs C during conveyance in the conveyor 10. The sensor 40 is an example of a detector in the water-containing substance detection device according to the present invention. The infrared camera 41 is an example of a temperature sensor of the detector in the water-containing substance detection device according to the present invention.

In the embodiment, an ejection port 12 of the conveyor 10 is disposed on the downstream side of the conveyor 10. Moreover, the sensor 40 is arranged near the ejection port 12. The sensor 40 detects a water-containing crumb CW in crumbs C on the surface 11 of the conveyor 10, near the ejection port 12 of the conveyor 10, on the downstream side of the ejection port 12 of the conveyor 10. The downstream side refers to the right side of the conveyor 19 (the ejection port 12 side) in FIG. 1, and the upstream side refers to the left side of the conveyor 10 (the side opposite to the ejection port 12).

Specifically, as illustrated in FIG. 1, the sensor 40 is arranged near the ejection port 12, and above the downstream side of the ejection port 12 of the conveyor 10. The sensor 40 detects a water-containing crumb CW in crumbs C passing through the ejection port 12 of the conveyor 10, which is arranged obliquely below the sensor 40. Moreover, a member near the ejection port 12 of the conveyor 10 also has a surface with the emittance of 0.50 or more.

In a conventional water-containing substance detection device, the sensor is arranged immediately above a conveyor. The sensor may malfunction due to the influence of water vapor evaporated from the conveyed crumbs that are subjected to the drying process, or the influence of heat from a heater, such as a hot air blower (to be described later). Moreover, when a processing amount for crumbs is great, the crumbs are conveyed overlapping vertically with each other, and crumbs at lower positions are not readily detected by the sensor arranged immediately above the conveyor. Thus, the detection accuracy may be degraded.

In the crumb detection device 100 according to the present embodiment, the sensor 40 is disposed on the downstream side of the ejection port 12 of the conveyor 10 (not disposed immediately above the conveyor 10). Thus, the sensor 40 is less influenced by water vapor evaporated from the conveyed crumbs that are subjected to the drying process, or by heat from a heater, such as a hot air blower (to be described later), thereby reducing the likelihood of malfunctions.

Moreover, the overlapping of the crumbs C gradually decreases during the conveyance, and the overlapping of the crumbs C tends to be small near the ejection port 12 of the conveyor 10, at which crumbs C fall. The tendency becomes noticeable when a vibration conveyor is employed. Thus, even when more crumbs C are conveyed, the detection accuracy is prevented from being degraded by detecting water-containing crumbs CW in the crumbs C near the ejection port 12 of the conveyor 10.

Furthermore, the surface 11 near the ejection port 12 of the conveyor 10 has an emissivity of 0.50 or more, and a reflection of light on the surface 11 near the ejection port 12 of the conveyor 10 is reduced. Thus, degradation in the detection accuracy of the sensor 40 may be reduced.

Moreover, in the crumb detection device 100 according to the embodiment, as illustrated in FIG. 1, a heater such as a hot air blower 20 for heating the conveyor 10 is preferably disposed. When the temperature of the surface 11 of the conveyor 10 is low, the sensor 40 may erroneously detect that the surface 11 of the conveyor 10 is a water-containing crumb CW. With the above-described hot air blower 20, the temperature of the surface 11 of the conveyor 10 is controlled to be constant. The hot air blower 20 is an example of the heater in the water-containing substance detection device according to the present invention. The above-described heater is not limited to be the hot air blower 20, and heating means other than the hot air blower 20 may be used.

According to the heating operation of the hot air blower 20, the maintained temperature of the surface 11 of the conveyor 10 preferably falls within a range of 30° C. to 70° C., more preferably falls within a range of 40° C. to 70° C., and further preferably falls within a range of 50° C. to 70° C. By controlling the temperature within the above-described ranges, the detection accuracy of the water-containing crumbs CW by the sensor 40 is enhanced. When the temperature of the surface 11 of the conveyor 10 is maintained at an extremely low temperature, the sensor 40 may erroneously detect the temperature, as described above. When the temperature of the surface 11 of the conveyor 10 is maintained at an extremely high temperature, a weighing accuracy in a bale formation may be degraded due to deterioration or mutual adhesion of products.

Moreover, in the present embodiment, in order to detect more accurately the conveyed crumbs C, a frame rate for recording infrared signals in the infrared camera 41 is changed according to the conveyance rate. The frame rate refers to a number of frames of a moving image, such as still images, processed in a unit of time. The frame rate of the infrared camera 41 falls within a range of 5 Hz to 120 Hz, preferably falls within a range of 9 Hz to 120 Hz, more preferably falls within a range of 15 Hz to 60 Hz, and further preferably falls within a range of 15 Hz to 33 Hz. When the frame rate is extremely great, a great arithmetic processing capacity is required, and it may take long time to detect water-containing crumb. When the frame rate is extremely small, a detection omission of crumbs C may occur.

Moreover, in the infrared camera 41, a thermal image resolution, required for recording infrared ray, depends on the smallest size of the crumb C to be detected, and a distance to the crumb C to be detected. Thus, the thermal image resolution of the infrared camera 41 preferably falls typically within a range of 80 (horizontal)×60 (vertical) to 1024×768, more preferably 160×120 or more, and further preferably 320×240 or more. When the thermal image resolution is extremely low, a water-containing crumb CW with small dimensions may not be detected. When the thermal image resolution is extremely high, it takes long time for processing signals, and the water-containing crumbs CW may not be removed in real time, which will be later in detail.

In the crumb detection device 100, a control device 50 including an arithmetic device, such as a personal computer, is provided. Moreover, in the control device 50 a display device 60 is arranged. The sensor 40 is connected to the control device 50. A signal detected by the sensor 40 is transmitted to the control device 50, and processed in the control device 50. In a processing method, a simple image may be used for detection. However, in order to avoid a duplicate detection of a crumb C, an image processing detecting a motion and a size of the crumb C is preferably performed. The processed image may be displayed on the display device 60. Signals inputted into the control device 50 and image data processed by the control device 50 may be recorded in a memory (not shown) incorporated in the control device 50, allowing data to be input and output.

The sensor 40 preferably includes a MOS (Metal Oxide Semiconductor) sensor 42, such as a digital camera, for capturing a real image of a water-containing crumb CW. The sensor 40 is preferably controlled so as to detect a size and a position of the water-containing crumb CW captured by the MOS sensor 42. By capturing the real image as described above, the size and the position of the water-containing crumb CW are specified, and thereby the detection accuracy of the water-containing crumb CW is enhanced. The MOS sensor 42 is an example of the image pickup included in the detector in the water-containing substance detection device according to the present invention. In the above-described image pickup, an imaging element such as, in addition to MOS sensor, a CMOS (Complementary Metal Oxide Semiconductor) sensor, or a CCD (Charge Coupled Device) may be used. From the point of view of a high processing rate and a high sensitivity, the CMOS sensor or the MOS sensor is preferably used.

From the point of view of performing more precise detection, the frame rate and a number of pixels that are greater than those in the infrared camera 41 are preferably used. Moreover, from the point of view of performing further precise detection, when the capturing of a real image is performed, a uniform irradiation without flickering using a white LED (not shown) or the like is preferably performed.

From the point of view of efficiently collecting water-containing crumbs CW, which will be described later, by precisely detecting a size, a position, a moving speed and the like of the water-containing crumbs CW, the image pickup, such as the above-described MOS sensor 42, is preferably used along with the temperature sensor such as the infrared camera 41.

Figure 2:
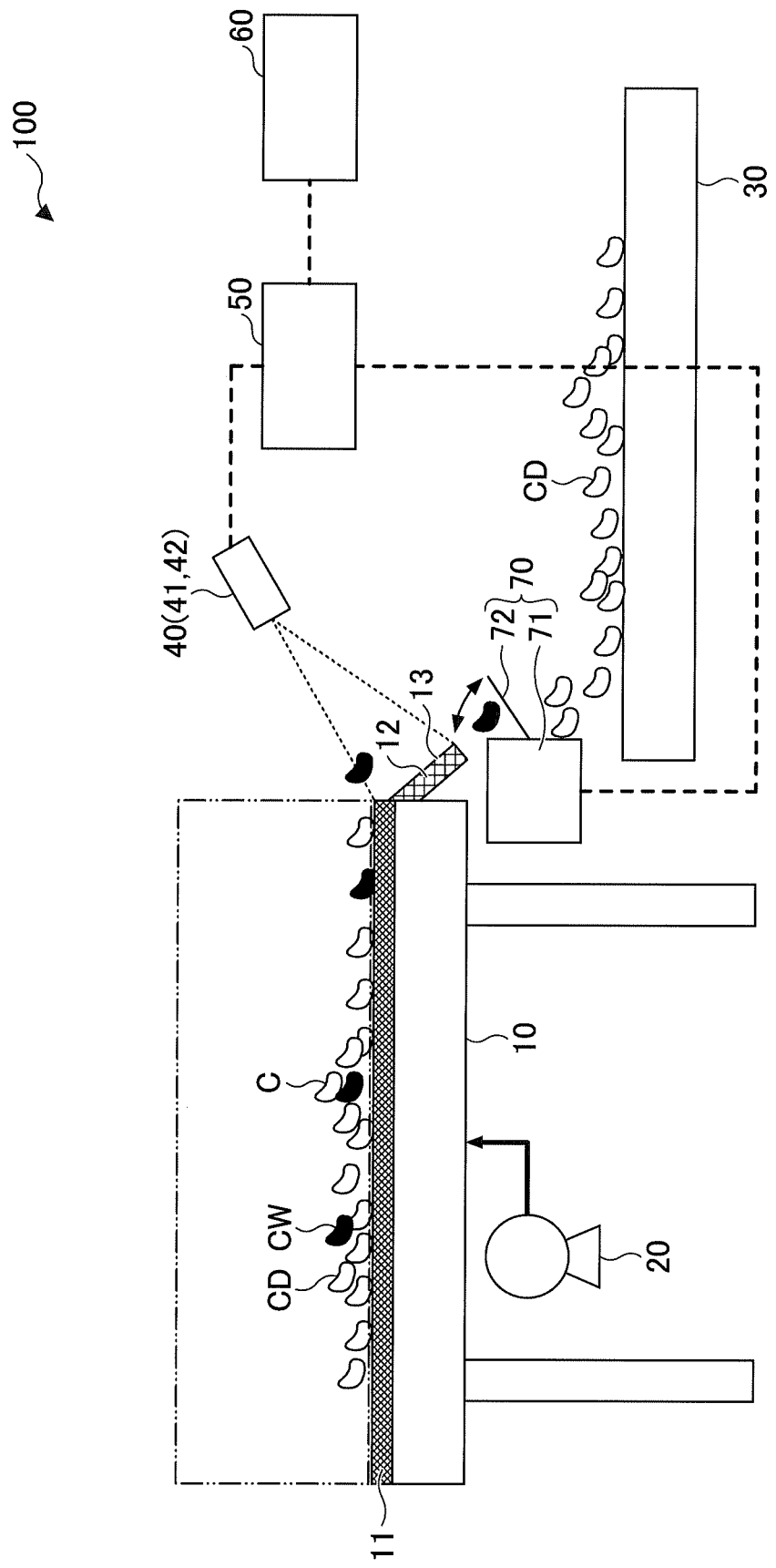
FIG. 2 is a diagram schematically depicting an example of a water-containing substance detection device according to a second embodiment of the present invention.

FIG. 2 is a diagram schematically depicting a crumb detection device 100 representing a water-containing substance detection device according to a second embodiment of the present invention. In the second embodiment, an inclined surface 13 that is inclined downward is arranged on an ejection port 12 side of a conveyor 10. The inclined surface 13 preferably has a surface 11 with an emissivity of 0.50 or more. A sensor 40 detects a water-containing crumb CW in crumbs C on the inclined surface 13. That is, in the crumb detection device 100 illustrated in FIG. 2, crumbs C fall along the inclined surface 13 from the ejection port 12 of the conveyor 10, and the falling crumbs C are detected by the sensor 40.

According to the above-described inclined surface 13, overlapping of the crumbs C is eliminated, and a water-containing crumb CW in the crumbs C is definitely detected. Moreover, the inclined surface 13 has the surface 11 with the emissivity of 0.50 or more, and a reflection of light on the surface 11 of the inclined surface 13 becomes small. Thus, the detection accuracy of the sensor 40 is prevented from being degraded.

Figure 3:
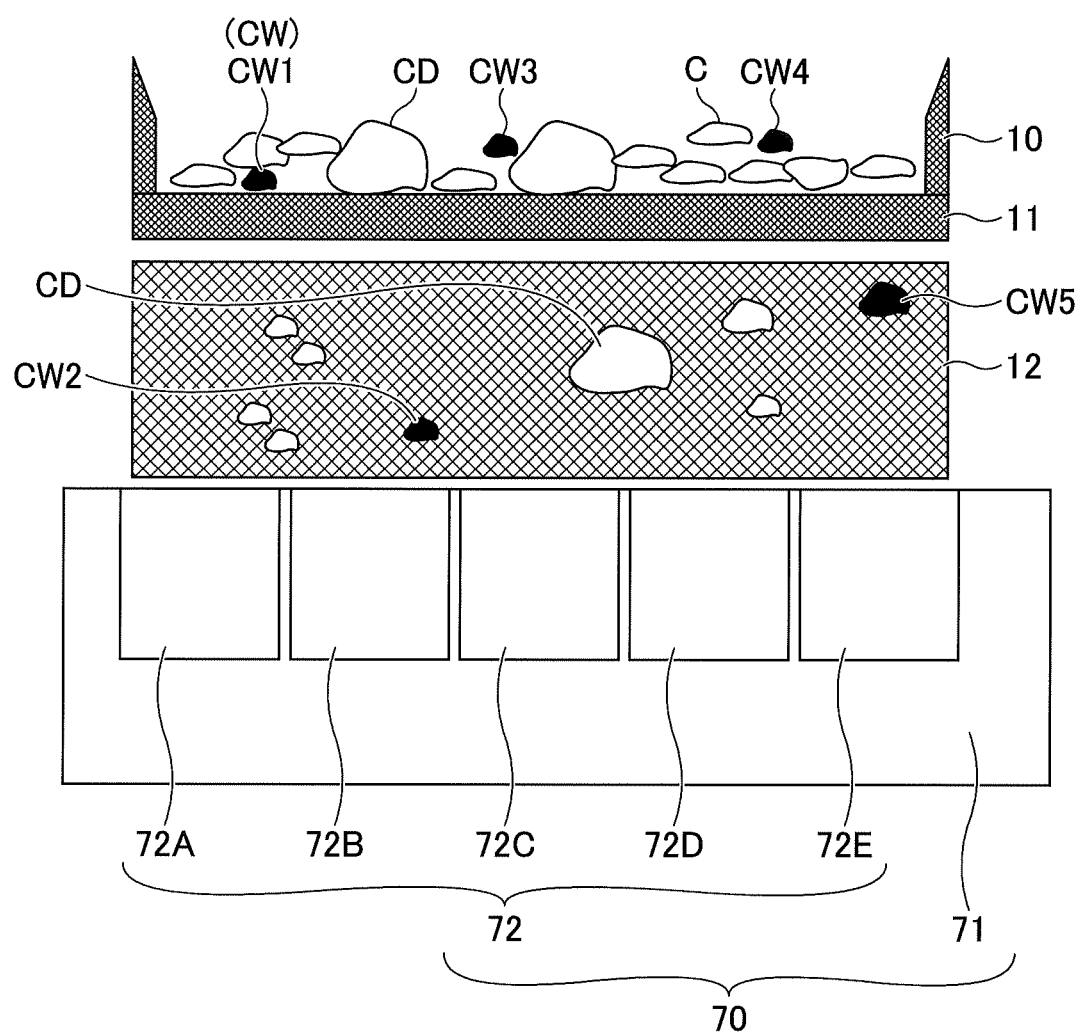
FIG. 3 is a diagram depicting an example of a collector in the water-containing substance detection device according to the embodiment of the present invention.

FIG. 3 is a diagram depicting the crumb detection device 100 according to the present application illustrated in FIG. 2, viewed from the downstream side of the conveyor 10 toward the upstream side. When water-containing crumbs CW are directly conveyed to the step of forming bales (also referred to as rubber bales), the water-containing crumbs may cause the degradation of quality of the bale. Thus, the detected water-containing crumbs CW are preferably collected. A method of collecting water-containing crumbs CW is not limited, and includes, for example, a method of blowing water-containing crumbs CW by air, a method of picking up water-containing crumbs by using robot arms, a method of removing water-containing crumbs, a method of removing by water-containing crumbs by using an opening and closing type chute, or the like. Shapes of crumbs C are not determined, and may be a large body, different from a resin pellet. Thus, the method of removing crumbs by using an opening and closing chute is preferable.

From the above-described point of view, in the present application, as illustrated in FIGS. 1 to 3, a collection box 70 for collecting water-containing crumbs CW is preferably arranged in the crumb detection device 100. The collection box 70 according to the embodiment of the present invention collects a water-containing crumb CW that is detected in crumbs C by the sensor 40.

The collection box 70 is arranged on the downstream side of the conveyor 10 (below the ejection port 12 of the conveyor 10, in FIGS. 1 and 2). Moreover, the collection box 70 preferably includes a storage unit 71 that stores collected crumb C; and a flap 72 that opens and closes as the crumb C are collected in the storage unit 71. The collection box 70 is an example of a collector in the water-containing substance detection device according to the present invention, and the flap 72 is an example of the opening-closing door of the collector.

The flap 72 of the collection box 70 is controlled to open, as illustrated in FIGS. 1 and 2, when the sensor 40 detects a water-containing crumb CW in crumbs C, so that the water-containing crumb CW is collected in the storage unit 71. When the sensor 40 does not detect a water-containing crumb CW in crumbs C, the flap 72 of the collection box 70 remains closed. Then, the crumbs C fall on the conveyor 30, and are conveyed to a section in which the process of forming bales is performed. The opening and closing operation of the flap 72 is controlled based on a signal from the sensor 40 controlled by the control device 50. According to the collection box 70, water-containing crumbs CW contained in the crumbs C after the drying process are further decreased. Thus, the quality of the bale formed by using the crumbs C is enhanced.

Moreover, the crumbs C containing the water-containing crumbs CW stored in the storage unit 71 of the collection box 70 may be returned to the upstream side of the conveyor 10 in the process of drying the crumbs C. In this case, a conveyer (not shown) that conveys the crumbs C to the upstream side of the conveyor 10 from the collection box 70 may be provided, and may be controlled to return the crumbs C to the upstream side of the conveyor 10. In this way, the crumbs C containing water-containing crumbs CW collected in the collection box 70 are dried again and detected by the sensor 40, and thereby water-containing crumbs CW contained in the crumbs C after the drying process are further decreased. The crumbs C collected in the collection box 70 are returned to the upstream side of the conveyor 10 controlled by the control device 50.

Moreover, the collection box 70 is controlled so as to open and close the flap 72 according to a size and a position of a water-containing crumb CW detected by the sensor 40 as illustrated in in FIG. 3. The operations of opening and closing the flap 72 are also controlled by the control device 50.

The flap 72 of the collection box 70 includes, as illustrated in FIG. 3, five flaps (flaps 72A to 72E). In the collection box 70, when the sensor 40 detects a size and a position of a water-containing crumb CW, the control device 50 calculates a size and a position in the width direction of the conveyor 10 of the water-containing crumb CW, and each of the flaps 72A to 72E is opened and closed based on the results of calculation.

Specifically, as illustrated in FIG. 3, when the sensor 40 detects each of water-containing crumbs CW1 to CW5, the flaps 72A to 72E are opened and closed, respectively, according to a size and a position in the width direction of the conveyor 10 of each of the water-containing crumbs CW1 to CW5, and thereby the water-containing crumbs CW1 to CW5 are collected into the storage unit 71 of the collection box 70.

In this way, by opening and closing the plurality of flaps 72A to 72E, only water-containing crumbs CW are controlled to be collected into the collection box 70, and dried crumbs CD are controlled not collected into the collection box 70. Thus, in the crumb detection device 100 according to the embodiment, the collection efficiency for water-containing crumbs CW is enhanced.

The crumb detection device 100 according to the embodiment detects a water-containing crumb CW in crumbs C with greater accuracy. Moreover, by collecting the water-containing crumb CW detected as above, a quality of a rubber product obtained from the crumbs C is enhanced.

Next, a crumb detection method according to the embodiment will be described. The crumb detection method according to the embodiment is a water-containing substance detection method for detecting a water-containing crumb CW in a plurality of crumbs C, and the above-described crumb detection device 100 is used.

Specifically, in the crumb detection method according to the embodiment, a plurality of crumbs C are conveyed by a conveyor 10; the crumbs C conveyed by the conveyor 10 are detected by a sensor 40; and the sensor 40 detects a water-containing crumb CW in the crumbs C on a downstream side of an ejection port 12, near the ejection port 12 of the conveyor 10 from which the crumbs fall (See FIG. 1). Moreover, an inclined surface 13 inclined downward may be arranged on the ejection port 12 side of the conveyor 10, so that a water-containing crumb CW in the crumbs C may be detected on the inclined surface 13 (See FIG. 2).

Moreover, the conveyer 10 has a surface 11 with an emissivity of 0.50 or more. The emissivity of the surface 11 of the conveyor 10 is preferably 0.70 or more, and further preferably 0.80 or more. Moreover, the conveyor 10 is preferably heated by a hot air blower 20.

For the sensor 40, an infrared camera 41 may be used (See FIG. 1). The frame rate of a temperature sensor falls within a range of 5 Hz to 120 Hz, preferably falls within a range of 9 Hz to 120 Hz, more preferably falls within a range of 15 Hz to 60 Hz, and further preferably falls within a range of 15 Hz to 33 Hz. Furthermore, the sensor 40 is preferably provided with a MOS sensor 42 for capturing a real image of a water-containing crumb CW, and preferably detects a size and a position of the water-containing crumb CW captured by the MOS sensor 42.

Furthermore, a collection box 70 for collecting the detected water-containing crumb CW is provided. When the sensor 40 detects a water-containing crumb CW in crumbs C, the water-containing crumb CW is collected in the collection box 70. The collection box 70 preferably includes a storage unit 71; and a flap that is opened and closed when a crumb C is collected in the storage unit 71. The flap 71 preferably includes a plurality of flaps 72A to 72E. Each of the flaps 72A to 72E is opened and closed according to a size and a position of the detected water-containing crumb CW.

When a water-containing crumb CW in crumbs C is detected by using the crumb detection method according to the embodiment, the effect of the crumb detection device 100 is obtained. That is, the water-containing crumb CW in the crumbs C is detected with greater accuracy. Moreover, by collecting the water-containing crumb CW detected as above, a quality of a rubber product obtained from the crumbs C is enhanced. The crumb detection method according to the embodiment is an example of a water-containing substance detection method according to the present invention.

Figure 4:
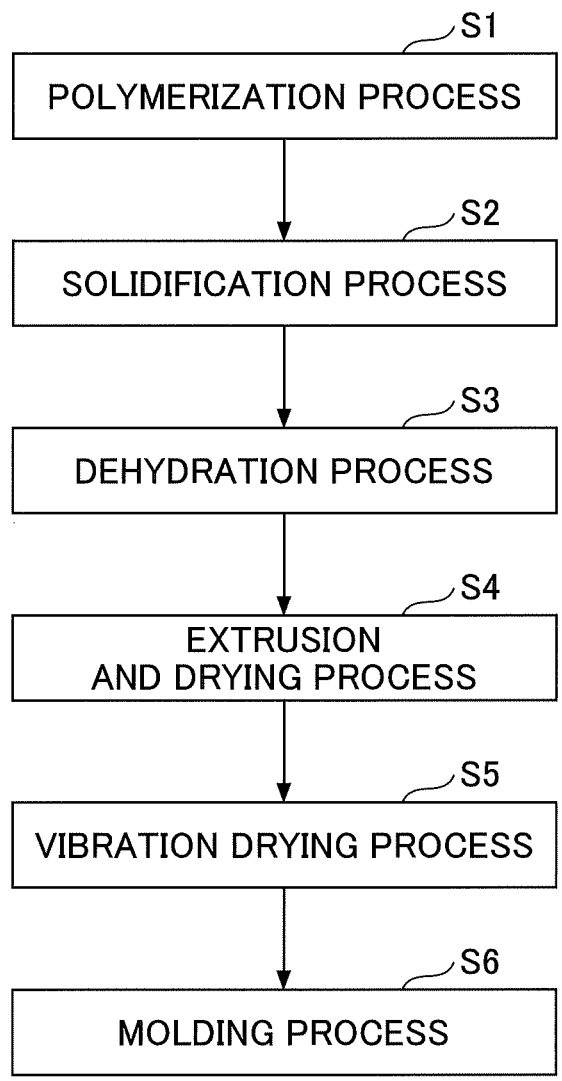
FIG. 4 is a flowchart schematically depicting an example of a method of manufacturing a rubbery polymer according to the embodiment of the present invention.

A method of manufacturing a rubbery polymer according to the embodiment will be described. FIG. 4 is a flowchart depicting an example of a method of manufacturing a rubbery polymer according to the embodiment of the present invention. As illustrated in FIG. 4, the method of manufacturing a rubbery polymer according to the embodiment includes a polymerization step S1; a solidification step S2; a dehydration step S3; an extrusion-drying step S4; a vibration-drying step S5; and a molding step S6. The method according to the embodiment is an example of a method of manufacturing a rubbery polymer according to the present invention.

In the polymerization step S1, a rubber raw material such as butadiene is polymerized by a polymerization reaction, such as a solution polymerization or an emulsion polymerization, to obtain a polymer solution or latex of a rubbery polymer. In the solidification step S2, the polymer solution or latex of a rubbery polymer is subjected to a solution removal process using a steam stripping method or a salt solidification, so that slurry of rubbery polymer is prepared. The solidification step S2 is an example of a solidification step in the method of manufacturing rubbery polymer according to the present invention.

In the dehydration step S3, the slurry of rubbery polymer is subjected to a dehydration process using a dehydrator, such as an extruder-type squeezer, to obtain crumbs having a prescribed water content. In the extrusion drying step S4, a dehydrated crumb C of rubbery polymer is subjected to an extrusion drying process, using an extrusion-type dryer. The dehydration step S3 and the extrusion drying step S4 are examples of a dehydration step and a crumbing step in the method of manufacturing a rubbery polymer according to the present invention.

In the vibration-drying step S5, the crumbs C after the extrusion drying step S4 are placed on a moving vibration belt; and heated while being vibrated and dried (in the following, referred to as "heat drying"). In the molding step S6, weights of the crumbs C after the vibration-drying step S5 are measured, and are molded into a bale with predetermined dimensions using a molding device. The bale has, for example, a rectangular parallelepiped shape with predetermined dimensions. The vibration-drying step S5 and the molding step S6 are examples of a vibration-drying step and a molding step in the method of manufacturing rubbery polymer according to the present invention, respectively.

The method of manufacturing rubbery polymer according to the embodiment further includes a conveyance step S51, an inspection step S52, and a collection step S54. These processes are performed by using the above-described crumb detection method according to the embodiment.

Figure 5:
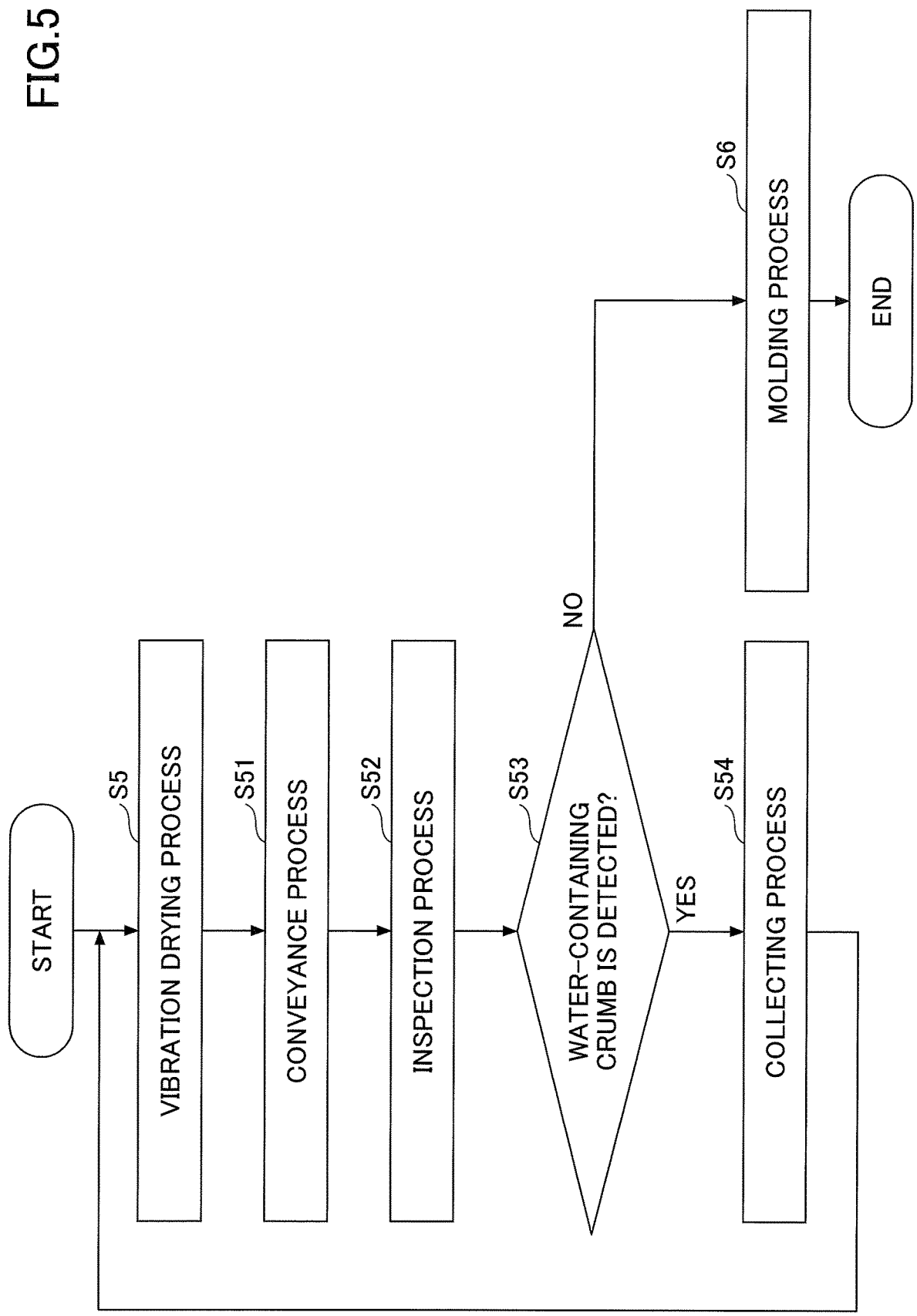
FIG. 5 is a flowchart schematically depicting an example of a method of detecting a water-containing substance according to the embodiment of the present invention.

In the method of manufacturing rubbery polymer according to the embodiment, as shown in FIG. 5, the conveyance step S1 is performed after the vibration-drying step S5. In the conveyance step S51, the crumbs C that were dried in the vibration drying step S5 are conveyed. Then, the process proceeds to the inspection step S52, and the sensor 40 detects a water-containing crumb CW in the crumbs C on the downstream side of the ejection port 12 of the conveyor 10, near the ejection port 12 of the conveyor 10 from which the crumbs C conveyed on the conveyor fall.

When the sensor 40 detects a water-containing crumb CW in the crumbs C in the inspection step S52, the process proceeds to the collection step S54, and the detected water-containing crumb CW is collected. Moreover, the collection step S54 includes a step of returning the collected water-containing crumb CW to the vibration-drying step S5 (step proceeding from S54 to S5). The collected water-containing crumb CW is conveyed to the vibration-drying step S5, and heated and dried again. The destination of the conveyance of the collected water-containing crumb CW is not limited to the vibration-drying step S5, and the collected water-containing crumb CW may be conveyed to the upstream side of the vibration-drying step S5 in which heating and drying is performed again.

Moreover, when in the inspection step S52 a water-containing crumb CW is not detected (S53), the process proceeds to the molding step S6, and the crumbs C are molded into a bale with predetermined dimensions.

According to the method of manufacturing the rubbery polymer according to the embodiment, the effect of the crumb detection method according to the embodiment is obtained. That is, a water-containing crumb CW in crumbs C is detected with greater accuracy. Moreover, by collecting the water-containing crumbs CW detected as above, the quality of the rubber product obtained from the crumbs C is enhanced.

EXAMPLES

The embodiment will be specifically described using practical examples. In the following, a "part" and a "percent (%)", unless otherwise specifically noted, are represented based on weight. Various tests and evaluations are performed according to the following methods.

[Preliminary Test (Detection Rate of Water-Containing Crumb)]

A preliminary test was performed for crumbs after the drying process (in the following, referred to as dried crumbs). Specifically, the dried crumbs are divided into completely dried crumbs and crumbs containing undried parts. About 20 kg of crumbs, preliminarily heated by an oven at 90° C. for 5 minutes were supplied so that the detection process was performed at a predetermined detection site of a bed of crumbs having a bed thickness of about 5 cm and a bed width of about 30 cm under a predetermined condition for three times. An average of the detection rates was set to a detection rate (%). In the following, dried rubber of about 20 kg will be obtained. Undried rubber contains a volatile content of about 20%. For the preliminary test, 100 bales each having a size of about 5 cm square and a thickness of about 1 cm were supplied.

[Removal Test of Water-Containing Crumb]

A test of removing the detected water-containing crumbs was performed. The removal test was performed by using the method of collecting crumbs C using the collection box 70 (See FIGS. 1 to 3). The removal test was also performed by using a method of blowing off using an air gun.

[Evaluation for Uniformity of Drying]

Bales molded from the obtained crumbs C were inspected continuously for one hour, and investigated whether a wet spot having a size of 10 mm or more was present on a surface of each of the bales. The wet spots were counted. The process of counting wet spots was performed two times, and an average value for 100 bales was obtained. When a wet spot was not found in the inspection for two hours in total, another 600 bales were continuously inspected, and 1000 bales were inspected in total. The average value of the number of wet spots for 100 bales was obtained from the results of inspection. From the average value, obtained as above, the uniformity of drying was evaluated. When the average value is one or less, the uniformity of drying was evaluated to be excellent. When the average value is greater than one, the average value is evaluated to be inferior in the uniformity of drying.

[Demonstration Test (Drying Method of Crumb)]

A solution of polymerized styrene butadiene rubber, in which a styrene content was 21%, an amount of vinyl in butadiene was 63 mol %, and having a Mooney viscosity of 45, was obtained in the usual manner using solution polymerization. After adding 0.2 parts of phenol-based antioxidants, solvent was removed by using a steam stripping method, and a dehydrating process was performed by using a continuously rotational screw extruder, to obtain crumbs of the rubbery polymer having a water content of 15% and a residual cyclohexane amount of 1.5%. The crumbs obtained as above were supplied into an extrusion dryer (actual machine) having a diameter of 14 inches, at a predetermined supply rate. A die temperature was maintained at 160° C., and the crumbs were dried. After the drying process in the extrusion dryer, the crumbs were further dried in additional three hot air drying sections. Then, the detection process was performed. The crumbs were dried on the vibration conveyor in a state in which the air temperature was gradually decreased such that the drying temperature in the first section was 105° C., the drying temperature in the second section was 90° C., and the drying temperature in the third section was 90° C.-80° C.-50° C. or 90° C.-80° C.-70° C. Exposure times of the crumbs in the first, second and third sections were 0.5 minutes, 2 minutes and 2 minutes, respectively.

In the following, practical examples and comparative examples will be described. A preliminary test was performed for the practical examples 1 to 12, and the comparative examples 1 to 6.

Practical Example 1

Butadiene rubber was prepared by the solution polymerization reaction using an organic lithium catalyst. The Mooney viscosity of the butadiene rubber was 50, and 9 mol % of butadiene has 1,2-coupling. Solvent was removed from the butadiene rubber by using a steam stripping method, dehydrated using a continuously rotating screw dehydrator, to thereby obtain a rubber having a volatile content of 12%. The rubber was supplied into an extrusion dryer, in which a rotation speed was controlled so that a die temperature was 145° C., and thereby crumbs C were obtained. The crumbs C were dried with hot air. After the hot air drying in the first section (temperature was 100° C., exposure time was 30 seconds), the volatile content or the crumbs C was 5%. Furthermore, the crumbs C were dried by hot air at a temperature of 100° C. in the second section, and a series of three temperatures at 100° C., 70° C., and 30 to 70° C. in the third section. The crumbs C were detected, as shown in FIG. 1, using an infrared (IR) camera 41 (pixel number was 320×240, frame rate was 33 Hz) as the sensor 40, and a vibration drying method using a vibration conveyor as the drying method, at the ejection port 12 of the conveyor 10. An emissivity of a surface 11 of the conveyor 10 was 0.55, and a temperature of the surface 11 of the conveyor 11 was 70° C. A detection rate of a water-containing crumb CW was 83%. TABLE 1 shows the above-described detection conditions and the detected results.

Practical Example 2

The crumbs C were detected in the same way as in the practical example 1, except that the emissivity of the surface 11 of the conveyor 10 was 0.96. The detection rate of a water-containing crumb CW was 90%. The detection conditions and the detected results are shown in TABLE 1.

Practical Example 3

The crumbs C were detected in the same way as in the practical example 2, except that the infrared camera 41 and a MOS sensor 42 were used as the sensor 40 (See FIG. 1). A real-image moving-picture recording camera with a resolution of 1280×720 and a frame rate of 30 fps (4/3 type MOS sensor) was used for the MOS sensor 42. The crumbs C were irradiated with light from a white LED as auxiliary light. The detection rate of a water-containing crumb CW was 95%. The detection conditions and the detected results are shown in TABLE 1.

Practical Example 4

The crumbs C were detected in the same way as in the practical example 3, except that an inclined surface 13 was arranged on the ejection port 12 side of the conveyor 10 and the crumbs C were detected on the inclined surface 13 (See FIG. 2). The detection rate of a water-containing crumb CW was 100%. The detection conditions and the detected results are shown in TABLE 1.

Practical Example 5

The crumbs C were detected in the same way as in the practical example 3, except that the temperature of the surface 11 of the conveyor 10 was set to 50° C. (See FIG. 2). The detection rate of a water-containing crumb CW was 100%. The detection conditions and the detected results are shown in TABLE 1.

Practical Example 6

The crumbs C were detected in the same way as in the practical example 3, except that the temperature of the surface 11 of the conveyor 10 was set to 40° C. (See FIG. 2). The detection rate of a water-containing crumb CW was 98%. The detection conditions and the detected results are shown in TABLE 1.

Practical Example 7

The crumbs C were detected in the same way as in the practical example 3, except that the temperature of the surface 11 of the conveyor 10 was set to 30° C. (See FIG. 2). The detection rate of a water-containing crumb CW was 88%. The detection conditions and the detected results are shown in TABLE 1.

Practical Example 8

The crumbs C were detected in the same way as in the practical example 5, except that the crumbs C were dried by using a conveyor belt instead of performing the vibration drying (See FIG. 2). The detection rate of a water-containing crumb CW was 100%. The detection conditions and the detected results are shown in TABLE 1.

Practical Example 9

The crumbs C were detected in the same way as in the practical example 2, except that the frame rate of the sensor 40 (infrared camera 41) was set to 9 Hz (See FIG. 1). The detection rate of a water-containing crumb CW was 71%. The detection conditions and the detected results are shown in TABLE 1.

Practical Example 10

The crumbs C were detected in the same way as in the practical example 9, except that the frame rate of the sensor 40 (infrared camera 41) was set to 15 Hz (See FIG. 1). The detection rate of a water-containing crumb CW was 89%. The detection conditions and the detected results are shown in TABLE 1.

Practical Example 11

The crumbs C were detected in the same way as in the practical example 9, except that the frame rate of the sensor 40 (infrared camera 41) was set to 25 Hz (See FIG. 1). The detection rate of a water-containing crumb CW was 100%. The detection conditions and the detected results are shown in TABLE 1.

Comparative Example 1

The crumbs C were detected in the same way as in the practical example 8, except that the infrared camera 41 was not used as the sensor 40, only the MOS sensor 42 was used as the sensor 40, the crumbs C were detected from right above the conveyor 10, and the temperature of the surface 11 of the conveyor 10 was set to 90° C. (See FIG. 6). The detection rate of a water-containing crumb CW was 6%. The detection conditions and the detected results are shown in TABLE 1.

Comparative Example 2

The crumbs C were detected in the same way as in the practical example 8, except that the crumbs C were detected from right above the conveyor 10, and the temperature of the surface 11 of the conveyor 10 was set to 90° C. (See FIG. 6). The detection rate of a water-containing crumb CW was 59%. The detection conditions and the detected results are shown in TABLE 1.

Comparative Example 3

The crumbs C were detected in the same way as in the practical example 8, except that only the infrared camera 41 was used as the sensor 40, the crumbs C were detected from right above the conveyor 10, and the temperature of the surface 11 of the conveyor 10 was set to 90° C. (See FIG. 6). The detection rate of a water-containing crumb CW was 55%. The detection conditions and the detected results are shown in TABLE 1.

Comparative Example 4

The crumbs C were detected in the same way as in the practical example 1, except that the emissivity of the surface 11 of the conveyor 10 was set to 0.12 (See FIG. 6). The detection rate of a water-containing crumb CW was 61%. The detection conditions and the detected results are shown in TABLE 1.

Comparative Example 5

The crumbs C were detected in the same way as in the practical example 1, except that the emissivity of the surface 11 of the conveyor 10 was set to 0.31 (See FIG. 6). The detection rate of a water-containing crumb CW was 63%. The detection conditions and the detected results are shown in TABLE 1.

Comparative Example 6

The crumbs C were detected in the same way as in the practical example 9, except that the frame rate of the sensor 40 (infrared camera 41) was set to 1 Hz (See FIG. 6). The detection rate of a water-containing crumb CW was 15%. The detection conditions and the detected results are shown in TABLE 1.

In the practical examples 4 and 8, a removal test of the detected water-containing crumb CW was performed. In the removal test using the collection box 70, an average removal rate was 95%. In the removal test by a method of blowing off using an air gun, even if air hits a crumb, in most cases the crumb only rotates and is not removed, and smaller crumbs around the crumb tend to be ejected. Thus, the average removal rate was about 30%.

TABLE 1

| | Sensor | Drying method | Detection site | Emissivity of conveyor surface (%) | Substrate temperature (° C.) | Detection rate (%) |
| --- | --- | --- | --- | --- | --- | --- |
| Practical example 1 | IR | Vibration | Ejection port | 0.55 | 70 | 83 |
| Practical example 2 | IR | Vibration | Ejection port | 0.96 | 70 | 90 |
| Practical example 3 | IR and real image camera | Vibration | Ejection port | 0.96 | 70 | 95 |
| Practical example 4 | IR and real image camera | Vibration | Inclined surface | 0.96 | 70 | 100 |
| Practical example 5 | IR and real image camera | Vibration | Inclined surface | 0.96 | 50 | 100 |
| Practical example 6 | IR and real image camera | Vibration | Inclined surface | 0.96 | 40 | 98 |
| Practical example 7 | IR and real image camera | Vibration | Inclined surface | 0.96 | 30 | 88 |
| Practical example 8 | IR and real image camera | Conveyor belt | Inclined surface | 0.96 | 50 | 100 |
| Practical example 9 | IR with 9 Hz | Vibration | Ejection port | 0.96 | 70 | 71 |
| Practical example 10 | IR with 15 Hz | Vibration | Ejection port | 0.96 | 70 | 89 |
| Practical example 11 | IR with 25 Hz | Vibration | Ejection port | 0.96 | 70 | 100 |
| Comparative example 1 | Real image camera | Conveyor belt | Above conveyor | 0.96 | 90 | 6 |
| Comparative example 2 | IR and real image camera | Conveyer belt | Above conveyor | 0.96 | 90 | 59 |
| Comparative example 3 | IR | Conveyor belt | Above conveyor | 0.96 | 90 | 55 |
| Comparative example 4 | IR | Vibration | Ejection port | 0.12 | 70 | 61 |
| Comparative example 5 | IR | Vibration | Ejection port | 0.31 | 70 | 63 |
| Comparative example 6 | IR with 1 Hz | vibration | Ejection port | 0.96 | 70 | 15 |

In the practical examples 4 and 8, a removal test of the detected water-containing crumb CW was performed. In the removal test using the collection box 70, the average removal rate was 95%. In the removal test by a method of blowing off using an air gun, even if air hits a crumb, in most cases the crumb only rotates and is not removed, and smaller crumbs around the crumb tend to be ejected. Thus, the average removal rate was about 30%.

An actual machine test was performed based on the detection conditions and results of detection for the practical examples 4 to 6, shown in TABLE 1. According to the actual machine test, dried crumbs were detected. Water-containing crumbs CW were removed from the dried crumbs. The uniformity of drying was evaluated for the obtained crumbs (Practical examples 12 to 17, and comparative example 7).

Practical Example 12

Crumbs were prepared by supplying rubber into an extrusion dryer (actual machine) at a supply rate of 7000 kg/h. The crumbs were dried by performing a vibration drying using a vibration conveyor (conveyance width was 1.5 m). Then, the crumbs C were detected, as shown in FIG. 2, using an infrared camera 41 and a MOS sensor 42, as a sensor 40. An emissivity of a surface 11 of a conveyor 10 was 0.96, a temperature of the surface 11 of the conveyor 10 was 50° C., and crumbs were removed by using a collection box 70 (including one flap) (See FIGS. 2 and 3). The crumbs were removed at a rate of 236 kg/h, and the uniformity of drying was 0.1. The detection conditions and the detected results are shown in TABLE 2.

Practical Example 13

The crumbs C were detected in the same way as in the practical example 12, except that crumbs were removed by using a collection box 70 (including five flaps) (See FIGS. 2 and 3). The crumbs were removed at a rate of 75 kg/h, and the uniformity of drying was 0.1. The detection conditions and the detected results are shown in TABLE 2.

Practical Example 14

The crumbs C were detected in the same way as in the practical example 13, except that the temperature of the surface 11 of the conveyor 10 was set to 70° C. (See FIGS. 2 and 3). The crumbs were removed at a rate of 92 kg/h and the uniformity of drying was 0.0. The detection conditions and the detected results are shown in TABLE 2.

Practical Example 15

The crumbs C were detected in the same way as in the practical example 14, except that the supply rate for supplying rubber into the extrusion dryer (actual machine) was 5000 kg/h (See FIGS. 2 and 3). The crumbs were removed at a rate of 221 kg/h, and the uniformity of drying was 0.0. The detection conditions and the detected results are shown in TABLE 2.

Practical Example 16

The crumbs C were detected in the same way as in the practical example 15, except that the crumbs were dried by performing the vibration drying using a vibration conveyor (conveyance width was 1.8 m), and crumbs were removed by using a collection box 70 (including six flaps) (See FIGS. 2 and 3). The crumbs were removed at a rate of 111 kg/h, and the uniformity of drying was 0.0. The detection conditions and the detected results are shown in TABLE 2.

Practical Example 17

The crumbs C were detected in the same way as in the practical example 16, except that the temperature of the surface 11 of the conveyor 10 was set to 40° C. (See FIGS. 2 and 3). The crumbs were removed at a rate of 48 kg/h, and the uniformity of drying was 1.0. The detection condition and the detected results are shown in TABLE 2.

Comparative Example 7

The crumbs C were processed in the same way as in the practical example 17, except that the crumbs C were not detected, and the removal process was not performed. The uniformity of drying was 52.0. The process conditions and the results of the process are shown in TABLE 2.

TABLE 2

| | Drying method/ width | Site of detection | Rate (kg/h) | Temperature for heating conveyor (° C.) | Removal method | Amount of removal (kg/h) | Uniformity of drying (bale/100 bales) |
|---|---|---|---|---|---|---|---|
| Practical example 12 | Vibration/ 1.5 m | Inclined surface | 7000 | 50 | One flap | 236 | 0.1 |
| Practical example 13 | Vibration/ 1.5 m | Inclined surface | 7000 | 50 | Five flaps | 75 | 0.1 |
| Practical example 14 | Vibration/ 1.5 m | Inclined surface | 7000 | 70 | Five flaps | 92 | 0.0 |
| Practical example 15 | Vibration/ 1.5 m | Inclined surface | 5000 | 70 | Five flaps | 221 | 0.0 |
| Practical example 16 | Vibration/ 1.8 m | Inclined surface | 5000 | 70 | Six flaps | 111 | 0.0 |
| Practical example 17 | Vibration/ 1.8 m | Inclined surface | 5000 | 40 | Six flaps | 48 | 1.0 |
| Comparative example 7 | Vibration/ 1.8 m | — | 7000 | 40 | — | — | 52.0 |

From TABLE 1, the detection rate of a water-containing crumb CW is found to be 65% or more when the emissivity of the surface 11 of the conveyor 10 is 0.50 or more; and a water-containing crumb CW in crumbs C is detected on the downstream side of the ejection port 12 of the conveyor 10, near the ejection port 12 by using the infrared camera 41 having a frame rate that falls within a range of 5 to 120 Hz (practical examples 1 to 11).

The detection rate is found to be less than 65% when at least one of the three conditions: the emissivity of the surface 11 of the conveyor 10 being 0.50 or more; the frame rate of the infrared camera 41 falling within a range of 5 to 120 Hz; and a water-containing crumb CW in crumbs C being detected near the ejection port 12 of the conveyor 10, on the downstream side of the ejection port 12, by the infrared camera 41, is not satisfied (comparative examples 1 to 6).

Moreover, from TABLE 2, the uniformity of drying is found to be excellent when the infrared camera 41 and the MOS sensor 42 are used as the sensor; crumbs C are detected on the inclined surface 13 of the conveyor 10; and a detected water-containing crumb CW is collected into the collection box 70 (practical examples 12 to 17). When the crumbs C are not detected and thus a water-containing crumb CW is not collected, the uniformity of drying is found to be inferior (comparative example 7).

From the above-described results, by using the crumb detection device 100 according to the embodiment, it was found that a water-containing substance in a rubbery polymer could be detected with greater accuracy, and the quality of the resulting rubbery polymer was enhanced.

Various embodiments of the present invention have been described above. However, the present invention is not limited to the described embodiments. Various variations and modifications that a person skilled in the art will comprehend may be made to the configurations and details of the present invention without deviating from the scope of the present invention.

The present application is based on and claims the benefit of priority of Japanese Priority Application No. 2017-69253 filed on Mar. 30, 2017, the entire contents of which are hereby incorporated by reference.

REFERENCE SIGNS LIST 100 crumb detection device
10 conveyor
11 surface
12 ejection port
13 inclined surface
20 hot air blower
40 sensor
41 infrared camera
42 MOS sensor
50 control device
60 display device
70 collection box
71 storage unit
72 flap
C crumb
CD dried crumb
CW water-containing crumb

What is claimed is:

1. A water-containing substance detection device that detects a water-containing rubbery polymer among rubbery polymers, comprising:
    a conveyor configured to convey the rubbery polymers, the conveyor having a surface with an emissivity of 0.50 or more;
    a detector configured to detect the water-containing rubbery polymer among the rubbery polymers, conveyed by the conveyor, by a temperature sensor, and
    an inclined surface arranged on an ejection port side of the conveyor, the inclined surface having a surface with an emissivity of 0.50 or more and a property of substantially eliminating overlapping of the rubbery polymers, and the inclined surface being inclined downward with respect to the conveyor,
    the temperature sensor having a frame rate falling within a range of 5 Hz to 120 Hz, and
    the detector detecting the water-containing rubbery polymer among the rubbery polymers on the inclined surface,
    wherein the detector includes a capturing unit configured to capture a real image of the water-containing rubbery polymer,
    wherein the detector detects a size and a position of the water-containing rubbery polymer captured by the capturing unit, and
    wherein a frame rate and a number of pixels in the capturing unit are greater than the frame rate and a number of pixels in the temperature sensor.

2. The water-containing substance detection device according to claim 1 further comprising:
    a heater configured to heat the conveyor.

3. The water-containing substance detection device according to claim 1 further comprising:
    a collector configured to collect the water-containing rubbery polymer, when the temperature sensor detects the water-containing rubbery polymer among the rubbery polymers.

4. The water-containing substance detection device according to claim 3,
    wherein the collector includes a plurality of doors, and
    wherein each of the doors opens and closes depending on a size and a position of the water-containing rubbery polymer detected by the detector.

5. A water-containing substance detection method for detecting a water-containing rubbery polymer comprising:
    conveying rubbery polymers by a conveyor having a surface with an emissivity of 0.50 or more to an inclined surface arranged on an ejection port side of the conveyor to thereby substantially eliminate overlapping of the rubbery polymers, the inclined surface having a surface with an emissivity of 0.50 or more, the inclined surface being inclined downward with respect to the conveyor;
    detecting the water-containing rubbery polymer among the rubbery polymers during being conveyed by the conveyor, by a temperature sensor having a frame rate falling within a range of 5 Hz to 120 Hz,
    the temperature sensor detecting the water-containing rubbery polymer among the rubbery polymers on the inclined surface,
    capturing a real image of the water-containing rubbery polymer, and
    detecting a size and a position of the captured water-containing rubbery polymer, wherein a frame rate and a number of pixels in capturing the real image are greater than the frame rate and a number of pixels in the temperature sensor.

6. The water-containing substance detection method according to claim 5 further comprising:

heating the conveyor.

7. The water-containing substance detection method according to claim 5 further comprising:

collecting a water-containing rubbery polymer into a collector, when the temperature sensor detects the water-containing rubbery polymer among the rubbery polymers.

8. The water-containing substance detection method according to claim 7, wherein the collector includes a plurality of doors, and wherein the water-containing substance detection method further comprising:

opening and closing each of the doors depending on a size and a position of the water-containing rubbery polymer detected by the temperature sensor.

9. A method of manufacturing a rubbery polymer including:

solidifying a polymer solution of rubbery polymer, to prepare a slurry of rubbery polymer;

dehydrating the slurry;

forming crumbs of rubbery polymer from the dehydrated slurry of rubbery polymer; and drying the crumbs of rubbery polymer, the method further comprising:

conveying the dried crumbs of rubbery polymer by a conveyor having a surface with an emissivity of 0.50 or more to an inclined surface arranged on an ejection port side of the conveyor to thereby substantially eliminate overlapping of the rubbery polymers, the inclined surface having a surface with an emissivity of 0.50 or more, and the inclined surface being inclined downward with respect to the conveyor;

detecting a water-containing crumb of rubbery polymer among the crumbs of rubbery polymer on the inclined surface, by a temperature sensor having a frame rate falling within a range of 5 Hz to 120 Hz;

capturing a real image of the water-containing rubbery polymer, and detecting a size and a position of the captured water-containing rubbery polymer, a frame rate and a number of pixels in capturing the real image being greater than the frame rate and a number of pixels in the temperature sensor; and collecting a water-containing crumb of rubbery polymer, when the water-containing crumb of rubbery polymer is detected among the crumbs of rubbery polymer by the temperature sensor.

10. The method of manufacturing a rubbery polymer according to claim 9 further comprising:

returning the collected water-containing crumb of rubbery polymer to the drying the crumbs of rubbery polymer.

* * * * *